United States Patent
Eitan et al.

(10) Patent No.: US 9,674,811 B2
(45) Date of Patent: Jun. 6, 2017

(54) METHODS, APPARATUS AND SYSTEMS FOR MEDICAL DEVICE COMMUNICATION, CONTROL AND LOCALIZATION

(75) Inventors: Boaz Eitan, Hofit (IL); Meged Ofer, Netanya (IL); Asher Bitan, Beit Hashminay (IL)

(73) Assignee: Q-CORE MEDICAL LTD., Netanya (IL)

( * ) Notice: Subject to any disclaimer, the term of this patent is extended or adjusted under 35 U.S.C. 154(b) by 288 days.

(21) Appl. No.: 13/978,538

(22) PCT Filed: Jan. 16, 2012

(86) PCT No.: PCT/IB2012/050192
§ 371 (c)(1),
(2), (4) Date: Jul. 7, 2013

(87) PCT Pub. No.: WO2012/095829
PCT Pub. Date: Jul. 19, 2012

(65) Prior Publication Data
US 2013/0279370 A1    Oct. 24, 2013

Related U.S. Application Data

(60) Provisional application No. 61/433,227, filed on Jan. 16, 2011.

(51) Int. Cl.
*H04L 12/28* (2006.01)
*H04W 64/00* (2009.01)
(Continued)

(52) U.S. Cl.
CPC ...... *H04W 64/003* (2013.01); *A61N 1/37282* (2013.01); *G01S 5/0231* (2013.01);
(Continued)

(58) Field of Classification Search
CPC .................................................. A61B 5/0002
See application file for complete search history.

(56) References Cited

U.S. PATENT DOCUMENTS 2,056,322 A   10/1936   Hoppe
2,393,838 A   1/1946    Tarbox
(Continued)

FOREIGN PATENT DOCUMENTS

DE   10118086 A1   7/2002
EP   0215249 A1   3/1987
(Continued)

OTHER PUBLICATIONS

U.S. Appl. No. 12/463,399 Official Action (Non-Final) dated Jul. 21, 2011 (15 pages).
(Continued)

*Primary Examiner* — Maharishi Khirodhar
(74) *Attorney, Agent, or Firm* — Vladimir Sherman; Professional Patent Solutions

(57) ABSTRACT

Disclosed is a medical device including a therapeutic component to provide one or more therapeutic functionalities during whilst in therapeutic mode, and may further enter into a device sleep mode (DSM), a transceiver configured to provide the medical device with wireless connectivity and which may further transition into a transceiver sleep mode (TSM) substantially concurrent with transition into DSM, the transceiver may intermittently transition between TSM and a scan mode, during which scan mode the transceiver may listen for a wireless packet addressed to the transceiver, and a localization module which may emit a discovery signal upon receipt of the wireless packet addressed to the transceiver.

11 Claims, 16 Drawing Sheets

(51) Int. Cl.
    *G01S 5/02*           (2010.01)
    *H04W 4/04*         (2009.01)
    *H04W 52/02*       (2009.01)
    *A61N 1/372*       (2006.01)
    *H04W 76/04*       (2009.01)
    *H04L 29/08*        (2006.01)

(52) U.S. Cl.
    CPC ........... *H04W 4/04* (2013.01); *H04W 52/028*
    (2013.01); *H04W 52/0216* (2013.01); *H04W*
    *52/0229* (2013.01); *H04L 67/12* (2013.01);
    *H04W 76/046* (2013.01)

(56) References Cited

U.S. PATENT DOCUMENTS

| | | |
|---|---|---|
| 2,743,898 A | 5/1956 | King |
| 2,981,115 A | 4/1961 | Beguin |
| 3,443,585 A | 5/1969 | Reinicke |
| 3,511,583 A | 5/1970 | Brown |
| 3,677,667 A | 7/1972 | Morrison |
| 3,778,195 A | 12/1973 | Bamberg |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,178,138 A | 12/1979 | Iles |
| 4,236,880 A | 12/1980 | Archibald |
| 4,270,532 A | 6/1981 | Franetzki et al. |
| 4,290,346 A | 9/1981 | Bujan |
| 4,320,781 A | 3/1982 | Bouvet et al. |
| 4,373,525 A | 2/1983 | Kobayashi |
| 4,450,375 A | 5/1984 | Siegal |
| 4,479,797 A | 10/1984 | Kobayashi et al. |
| 4,489,863 A | 12/1984 | Horchos et al. |
| 4,493,706 A | 1/1985 | Borsanyi et al. |
| 4,650,469 A | 3/1987 | Berg et al. |
| 4,671,792 A | 6/1987 | Borsanyi |
| 4,682,135 A | 7/1987 | Yamakawa |
| 4,690,673 A | 9/1987 | Bloomquist |
| 4,725,205 A | 2/1988 | Cannon et al. |
| 4,728,265 A | 3/1988 | Cannon |
| 4,741,736 A | 5/1988 | Brown |
| 4,748,003 A | 5/1988 | Riley |
| 4,755,168 A | 7/1988 | Romanelli et al. |
| 4,836,752 A | 6/1989 | Burkett |
| 4,867,744 A | 9/1989 | Borsanyi |
| 4,893,991 A | 1/1990 | Heminway et al. |
| 4,927,411 A | 5/1990 | Pastrone et al. |
| 4,954,046 A | 9/1990 | Irvin et al. |
| 4,954,256 A | 9/1990 | Degen et al. |
| 4,978,335 A | 12/1990 | Arthur, III |
| 5,074,756 A | 12/1991 | Davis |
| 5,078,683 A | 1/1992 | Sancoff et al. |
| 5,088,904 A | 2/1992 | Okada |
| 5,096,385 A | 3/1992 | Georgi et al. |
| 5,103,211 A | 4/1992 | Daoud et al. |
| 5,151,019 A | 9/1992 | Danby et al. |
| 5,152,680 A | 10/1992 | Okada |
| 5,165,874 A | 11/1992 | Sancoff et al. |
| 5,213,483 A | 5/1993 | Flaherty et al. |
| 5,219,327 A | 6/1993 | Okada |
| 5,222,946 A | 6/1993 | Kamen |
| 5,246,347 A | 9/1993 | Davis |
| 5,257,978 A | 11/1993 | Haber et al. |
| 5,286,176 A | 2/1994 | Bonin |
| 5,290,158 A | 3/1994 | Okada |
| 5,308,333 A | 5/1994 | Skakoon |
| 5,338,157 A | 8/1994 | Blomquist |
| 5,395,320 A | 3/1995 | Padda et al. |
| 5,429,485 A | 7/1995 | Dodge |
| 5,485,408 A | 1/1996 | Blomquist |
| 5,499,969 A | 3/1996 | Beuchat et al. |
| 5,509,439 A | 4/1996 | Tantardini |
| 5,527,295 A | 6/1996 | Wing |
| 5,542,826 A | 8/1996 | Warner |
| 5,569,188 A | 10/1996 | Mackool |
| 5,575,309 A | 11/1996 | Connell |
| 5,575,631 A | 11/1996 | Jester |
| 5,577,891 A | 11/1996 | Loughnane et al. |
| 5,584,667 A | 12/1996 | Davis |
| 5,593,134 A | 1/1997 | Steber et al. |
| 5,601,420 A | 2/1997 | Warner et al. |
| 5,628,619 A | 5/1997 | Wilson |
| 5,658,250 A | 8/1997 | Blomquist et al. |
| 5,658,252 A | 8/1997 | Johnson |
| 5,660,529 A | 8/1997 | Hill |
| 5,669,877 A | 9/1997 | Blomquist |
| 5,683,233 A | 11/1997 | Moubayed et al. |
| 5,695,473 A | 12/1997 | Olsen |
| 5,704,584 A | 1/1998 | Winterer et al. |
| 5,742,519 A | 4/1998 | McClendon et al. |
| 5,782,805 A | 7/1998 | Meinzer et al. |
| 5,788,669 A | 8/1998 | Peterson |
| 5,791,880 A | 8/1998 | Wilson |
| 5,791,881 A | 8/1998 | Moubayed et al. |
| 5,803,712 A | 9/1998 | Davis et al. |
| 5,807,322 A | 9/1998 | Lindsey et al. |
| 5,810,323 A | 9/1998 | Winterer et al. |
| 5,853,386 A | 12/1998 | Davis et al. |
| 5,876,370 A | 3/1999 | Blomquist |
| 5,888,052 A | 3/1999 | Hill |
| 5,896,076 A | 4/1999 | Van Namen |
| 5,909,724 A | 6/1999 | Nishimura et al. |
| 5,924,852 A | 7/1999 | Moubayed et al. |
| 5,935,099 A | 8/1999 | Peterson et al. |
| 5,935,106 A | 8/1999 | Olsen |
| 5,943,633 A | 8/1999 | Wilson et al. |
| 5,954,485 A | 9/1999 | Johnson et al. |
| 5,980,490 A | 11/1999 | Tsoukalis |
| 5,996,964 A | 12/1999 | Ben-Shalom |
| 6,024,539 A | 2/2000 | Blomquist |
| 6,095,189 A | 8/2000 | Ben-Shalom |
| 6,110,153 A | 8/2000 | Davis et al. |
| 6,146,109 A | 11/2000 | Davis et al. |
| 6,164,921 A | 12/2000 | Moubayed et al. |
| 6,165,874 A | 12/2000 | Powell et al. |
| RE37,074 E | 2/2001 | Danby et al. |
| 6,203,296 B1 | 3/2001 | Ray et al. |
| 6,213,723 B1 | 4/2001 | Danby et al. |
| 6,213,739 B1 | 4/2001 | Phallen et al. |
| 6,234,773 B1 | 5/2001 | Hill et al. |
| 6,241,704 B1 | 6/2001 | Peterson et al. |
| 6,261,262 B1 | 7/2001 | Briggs et al. |
| 6,280,408 B1 | 8/2001 | Sipin |
| 6,312,227 B1 | 11/2001 | Davis |
| 6,339,410 B1 | 1/2002 | Milner et al. |
| 6,347,553 B1 | 2/2002 | Morris et al. |
| 6,371,732 B1 | 4/2002 | Moubayed et al. |
| 6,422,057 B1 | 7/2002 | Anderson |
| 6,450,773 B1 | 9/2002 | Upton |
| 6,475,180 B2 | 11/2002 | Peterson et al. |
| 6,519,569 B1 | 2/2003 | White et al. |
| 6,537,244 B2 | 3/2003 | Paukovits et al. |
| 6,544,171 B2 | 4/2003 | Beetz et al. |
| 6,558,347 B1 | 5/2003 | Jhuboo et al. |
| 6,572,604 B1 | 6/2003 | Platt et al. |
| 6,622,542 B2 | 9/2003 | Derek et al. |
| 6,648,861 B2 | 11/2003 | Platt et al. |
| 6,692,241 B2 | 2/2004 | Watanabe et al. |
| 6,733,476 B2 | 5/2004 | Christenson et al. |
| 6,742,992 B2 | 6/2004 | Davis |
| 6,749,587 B2 | 6/2004 | Flaherty |
| 6,768,425 B2 | 7/2004 | Flaherty et al. |
| 6,788,199 B2 * | 9/2004 | Crabtree et al. ......... 340/539.13 |
| 6,790,198 B1 | 9/2004 | White et al. |
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |

(56) References Cited

U.S. PATENT DOCUMENTS

| | | |
|---|---|---|
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1* | 9/2005 | Tanner et al. ............. 417/477.2 |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1* | 2/2007 | Bowles et al. ................. 439/11 |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1* | 6/2008 | Jia et al. ....................... 370/312 |
| 2008/0145249 A1 | 6/2008 | Smisson et al. |
| 2008/0146995 A1 | 6/2008 | Smisson et al. |
| 2008/0157970 A1* | 7/2008 | Single ................... G01S 5/0263 340/572.1 |
| 2008/0275307 A1* | 11/2008 | Poschmann ................. 600/300 |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | Debelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0198280 A1* | 8/2010 | Corndorf ........... A61N 1/37276 607/3 |
| 2010/0211002 A1 | 8/2010 | Davis |
| 2010/0228223 A1 | 9/2010 | Williams et al. |
| 2010/0234708 A1* | 9/2010 | Buck et al. .................... 600/365 |
| 2010/0279652 A1 | 11/2010 | Sharp et al. |
| 2011/0148624 A1* | 6/2011 | Eaton et al. ............. 340/539.13 |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1* | 3/2012 | Larson et al. ................. 606/129 |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1* | 2/2015 | Ho et al. ....................... 455/509 |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |

(56) References Cited

FOREIGN PATENT DOCUMENTS

| | | | |
|---|---|---|---|
| EP | 0483794 | A1 | 5/1992 |
| EP | 0858812 | A2 | 8/1998 |
| EP | 1031358 | A1 | 8/2000 |
| EP | 1350955 | A2 | 10/2003 |
| EP | 1557186 | | 7/2005 |
| EP | 1611834 | A2 | 1/2006 |
| EP | 1485149 | B1 | 7/2008 |
| FR | 2632529 | A1 | 12/1989 |
| FR | 2753236 | A1 | 3/1998 |
| JP | 60043188 | A | 3/1985 |
| JP | 6-169992 | A | 6/1994 |
| JP | 2002-57738 | A | 2/2002 |
| JP | 2004141418 | A | 5/2004 |
| WO | 8400691 | A1 | 3/1984 |
| WO | 9116933 | A1 | 11/1991 |
| WO | 9325816 | A1 | 12/1993 |
| WO | 9408647 | A1 | 4/1994 |
| WO | 9603168 | A1 | 2/1996 |
| WO | 9630679 | A1 | 10/1996 |
| WO | 9734084 | A1 | 9/1997 |
| WO | 9804301 | A1 | 2/1998 |
| WO | 9813080 | A2 | 4/1998 |
| WO | 9847551 | A1 | 10/1998 |
| WO | 99/58178 | A1 | 11/1999 |
| WO | 0139816 | A2 | 6/2001 |
| WO | 0165232 | A1 | 9/2001 |
| WO | 0236044 | A2 | 5/2002 |
| WO | 0238204 | A2 | 5/2002 |
| WO | 0249509 | A2 | 6/2002 |
| WO | 02068015 | A2 | 9/2002 |
| WO | 03027503 | A1 | 4/2003 |
| WO | 03080158 | A1 | 10/2003 |
| WO | 2004070548 | A2 | 8/2004 |
| WO | 2004093648 | A2 | 11/2004 |
| WO | 2005089263 | A2 | 9/2005 |
| WO | 2006/056986 | A1 | 6/2006 |
| WO | 2007133259 | A1 | 11/2007 |
| WO | 2008036658 | A2 | 3/2008 |
| WO | 2008059492 | A2 | 5/2008 |
| WO | 2008059493 | A2 | 5/2008 |
| WO | 2008059494 | A2 | 5/2008 |
| WO | 2008059495 | A2 | 5/2008 |
| WO | 2008059496 | A2 | 5/2008 |
| WO | 2008059498 | A2 | 5/2008 |
| WO | 2008059499 | A2 | 5/2008 |
| WO | 2008130644 | A1 | 10/2008 |
| WO | 2010053702 | A1 | 5/2010 |
| WO | 2010053703 | A1 | 5/2010 |
| WO | 2010091313 | A2 | 8/2010 |
| WO | 2011128850 | A2 | 10/2011 |
| WO | 2012095827 | A1 | 7/2012 |
| WO | 2012095829 | A2 | 7/2012 |
| WO | 2013001425 | A2 | 1/2013 |
| WO | 2013/028704 | A1 | 2/2013 |
| WO | 2013/090748 | A1 | 6/2013 |

OTHER PUBLICATIONS

U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).
International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).

(56) References Cited

OTHER PUBLICATIONS

International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).

Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
European Application No. 05810500.8 Official Action dated Nov. 3, 2014 (5 pages).
European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).

(56) References Cited

OTHER PUBLICATIONS

U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).

* cited by examiner

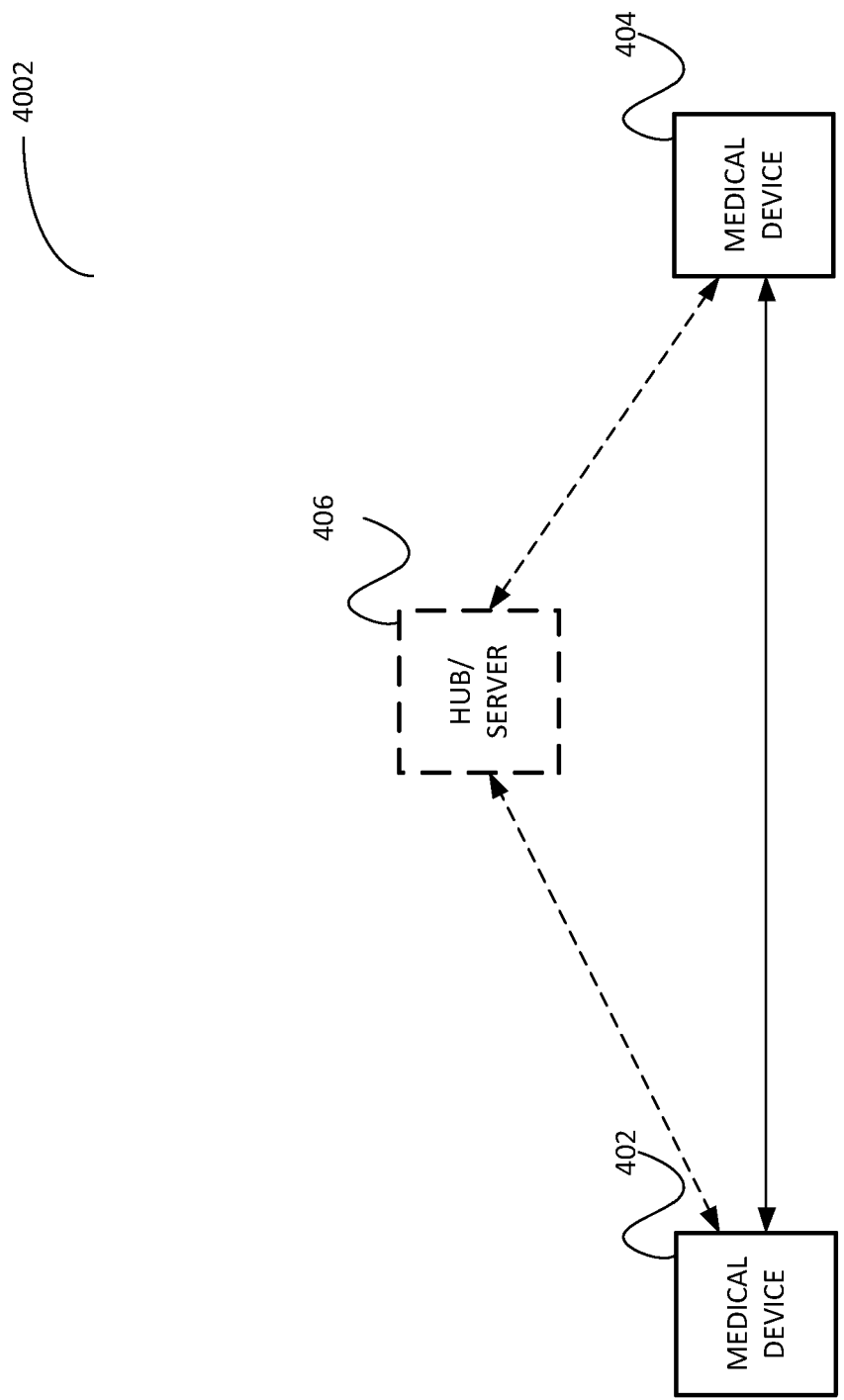

METHODS, APPARATUS AND SYSTEMS FOR MEDICAL DEVICE COMMUNICATION, CONTROL AND LOCALIZATION

CROSS-REFERENCE TO RELATED APPLICATIONS

U.S. patent application Ser. No. 13/978,538, is a U.S. National Stage application of International Application PCT/IB2012/050192, filed on Jan. 16, 2012 by the inventors of the present application and titled: "METHODS, APPARATUS AND SYSTEMS FOR MEDICAL DEVICE COMMUNICATION, CONTROL AND LOCALIZATION"; International Application PCT/IB2012/050192 claims the benefit of U.S. Provisional Application No. 61/433,227, filed on Jan. 16, 2011.

FIELD OF THE INVENTION

The present invention relates generally to the field of wireless connectivity of medical devices. More specifically, the present invention relates to methods, apparatus and systems for wireless medical device communication, control and localization.

BACKGROUND

Medical devices operate for therapeutic and/or diagnostic uses such as peristaltic pumps which may be used to infuse medicines into a vein, blood pressure monitors which may monitor a patient's blood pressure and heart rate, electrical thermometers which may measure a patient's body temperature and many more.

A medical device may be used in a hospital, doctor or nurse's office or other medical treatment centers. Medical devices may also be used at patient's homes or personal environments.

Medical devices may be sought for example if they are misplaced, lost, for inventory purposes, when the medical device needs to be updated and more.

SUMMARY OF THE INVENTION

The present invention includes methods, apparatus and systems for medical device communication, control and localization. According to some embodiments of the present invention, there may be provided a medical device including a controller adapted to facilitate intermittent transitions of the device from a sleep mode into a scan mode during which scan mode a transceiver of the medical device is at least partially activated. During scan mode the controller may cause the transceiver to: (1) wirelessly transmit/broadcast its own identifier, (2) listen for wireless packets addressed to the transceiver identifier, and (3) wirelessly connect to and check a registry of a computing platform. According to further embodiments the controller may monitor the transceiver output for an activation event. In the absence of an activation event, the controller may deactivate the transceiver transition to sleep mode for some period of time before initiating another scan mode. In the presence of an activation event, the controller may activate additional portions of the medical device. Depending upon the specific nature of the activation event, the controller may activate: (1) a beacon and/or (2) a signal of the medical device According to some embodiments, a computing platform may include a wireless transceiver and may scan for one or more medical devices. Upon detection of the medical devices the computing platform may: (1) Identify/Receive a location of the medical device (2) control the medical device or cause the medical device to emit a beacon (3) facilitate wireless update of the medical device (update firmware, update operational modes, update drug libraries and more) and/or (4) facilitate wireless coordination between multiple medical devices.

According to some embodiments the computing platform may be a second medical device, one or more hot spots associated with a server or central management control computer, a moving hot spot or a hand held/mobile device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4A-4E are schematic illustrations, depicting exemplary medical device communication, control and localization systems according to embodiments of the present invention;

Figure 1A:
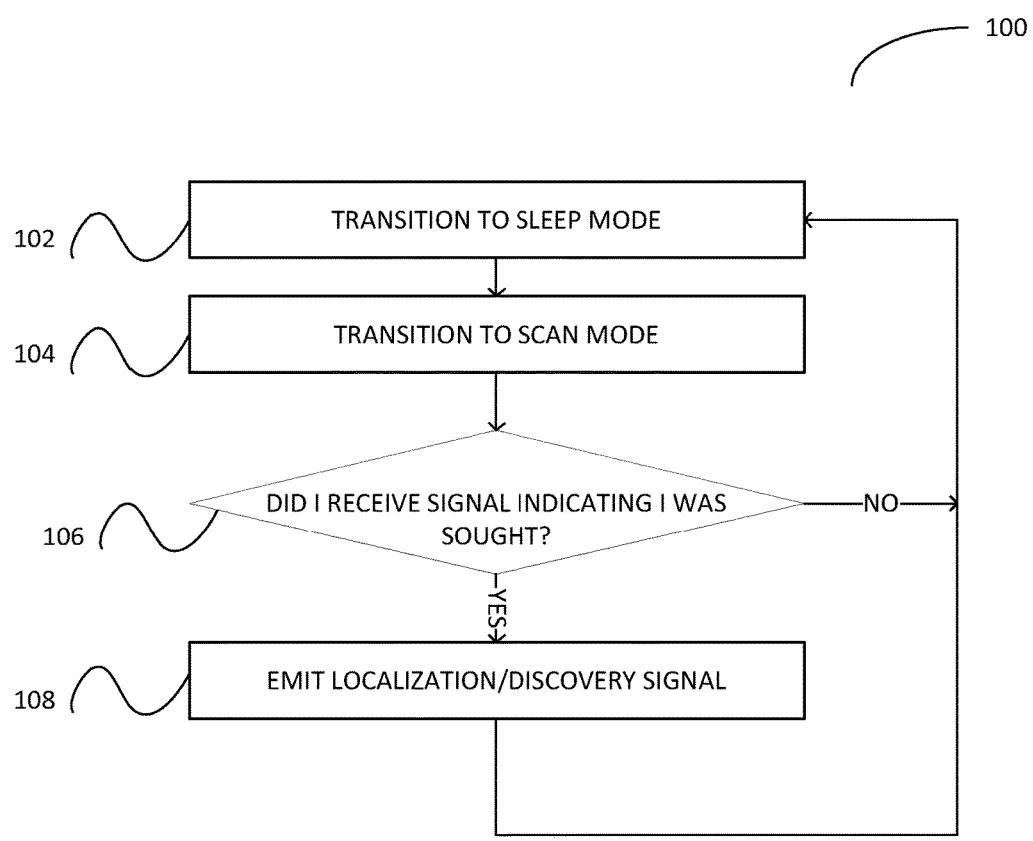
FIG. 1A-1E are flowcharts including the exemplary steps associated with which may be performed by exemplary medical devices according to the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

A medical device communication system may perform or aid in localizing, monitoring, controlling, updating one or more medical device as well as coordinating between two or more medical devices.

According to some embodiments, medical devices may be dispersed across a healthcare facility or may be located remotely such as offsite, at a patient residence or otherwise. Localizing, estimating coordinates or location of a medical device may be advantageous when a device is being sought. Localizing a medical device may further trigger a beacon on a device being sought, further assisting in finding the device. For example, a medical device being sought within a ward of a hospital may be localized and a beacon triggered on the device may assist in finding the device even when it is in a closet or out of sight.

According to some embodiments, a medical device communication system may maintain accurate monitoring of one or more medical devices dispersed across a healthcare facility and/or located remotely (such as offsite, at a patient residence and more). Accurate monitoring may aid in managing medical device inventory and improve attrition rates stemming from lost or misplaced medical devices.

According to some embodiments, a medical device communication system may enable wireless control of one or more medical devices dispersed across a healthcare facility and/or located remotely. Wireless control of a medical device may enable administering treatment remotely.

According to some embodiments, a medical device communication system may facilitate updating of medical devices dispersed across a healthcare facility and/or located remotely. Update of medical devices may include: firmware, operation modes or regimes and update of drug libraries associated with a medical device and more. Update of medical devices may be improved by a wireless update, thus removing the need to physically reach each medical device in order to carry out update of the medical device. Furthermore, the medical device communication may include detection or localization of the medical devices before updating them.

According to some embodiments, a medical device communication system may facilitate wireless coordination between multiple (two or more) medical devices servicing a given patient or set of patients. For example, two or more medical devices such as pumps administering medication to a patient may be correlated so that the treatment is administered in coordination to achieve optimal administration.

According to some embodiments, a medical device may include a therapeutic component adapted to provide therapeutic functionality during whilst in therapeutic mode and further adapted to enter a device sleep mode (DSM); a transceiver may be configured to provide the device with wireless connectivity and may further be configured to transition into a transceiver sleep mode (TSM) substantially concurrent with transition into DSM. The transceiver may further be configured to intermittently transition between TSM and a scan mode, during which scan mode the transceiver may listen for a wireless packet addressed to the transceiver; and a localization module configured to emit a discovery signal upon receipt of said wireless packet addressed to said transceiver.

According to some embodiments, a medical device may include a therapeutic component adapted to provide therapeutic functionality during whilst in therapeutic mode and further adapted to enter a device sleep mode (DSM); a transceiver may be configured to provide the device with wireless connectivity and may further be configured to transition into a transceiver sleep mode (TSM) substantially concurrent with transition into DSM. The transceiver may further be configured to intermittently transition between TSM and a scan mode, during which scan mode the transceiver may intermittently transmits a wireless packet identifying the transceiver. The medical device may further include a localization module configured to emit a discovery signal upon receipt of a confirmation from a seeking device.

According to some embodiments, substantially upon receipt of the wireless packet, the transceiver may be configured to transition to an awake mode and the therapeutic component may be configured to transition into a therapeutic mode.

According to some embodiments, the medical device may further include a screen which may display a flag indicative of a non-discovery condition.

According to some embodiments, the therapeutic component may be configured to receive an update via the transceiver.

According to some embodiments, the therapeutic component may be configured to transition into a slave mode and to be remotely operated by a master device via the transceiver.

According to some embodiments, the medical device may further include a battery whose full charge capacity and passive discharge rate ratio may be above a threshold value, wherein the ratio threshold is selected such that a battery of the selected type is operative to support the transceiver operation for at least 4 months.

According to some embodiments, the therapeutic component may be a peristaltic pump.

According to some embodiments, a method for localizing a medical device including a transceiver may include receiving an identifier from a medical device at one or more computing platforms, determining an estimated location of the medical device based on secondary information from the one or more computing platforms, seeking the medical device in proximity to the estimated location, hearing a beacon from the medical device and locating the medical device According to some embodiments, the method may further include confirming a discovery.

According to some embodiments, determining an estimated location may be carried out based on antenna triangulation, look up table and/or computing platform location.

Turning now to FIG. 1A-1E, depicted are flowcharts including the exemplary steps associated with which may be performed by exemplary medical devices according to the present invention.

According to some embodiments, a method for localizing a medical device may be carried out such as method 100 of FIG. 1A. A medical device may be in a sleep, idle, standby or non-active mode, for example, when it is not in use or has concluded administering a treatment (as shown in step 102). Sleep, idle, standby or non-active modes may assist in saving power and lengthening battery life and lowering the frequency in which the medical device needs to be plugged into a socket in order to recharge batteries. The medical device may switch to a scanning mode (as shown in step 104) in which scanning circuitry such as transceivers, controllers and more may be activated. While in scanning mode the medical device may continuously or intermittently listen or await receipt of a poll or signal from a seeking device (as shown in step 106). Receipt of a poll may cause/trigger a localization module within the medical device to emit a localization/discovery signal to aid or assist in detection of the medical device such as a beacon, an alarm, a light or a location indicative signal in response to the poll (as shown in step 108). If no poll or seeking signal were received within a predetermined length of time the medical device may transition back to sleep mode (returning to step 102). The medical device may transition between sleep mode (step 102) and scan mode (step 104) intermittently based on fixed, predetermined periods or may transition according to variable periods depending on secondary parameters such as an internal clock or a preprogrammed schedule. For example, the medical device may transition between sleep mode (step 102) and scan mode (step 104) once every 5 minutes during the day and once every hour at night which may be defined as a period with a lower likelihood to receive a wireless packet from a seeking device (step 106).

Figure 1B:
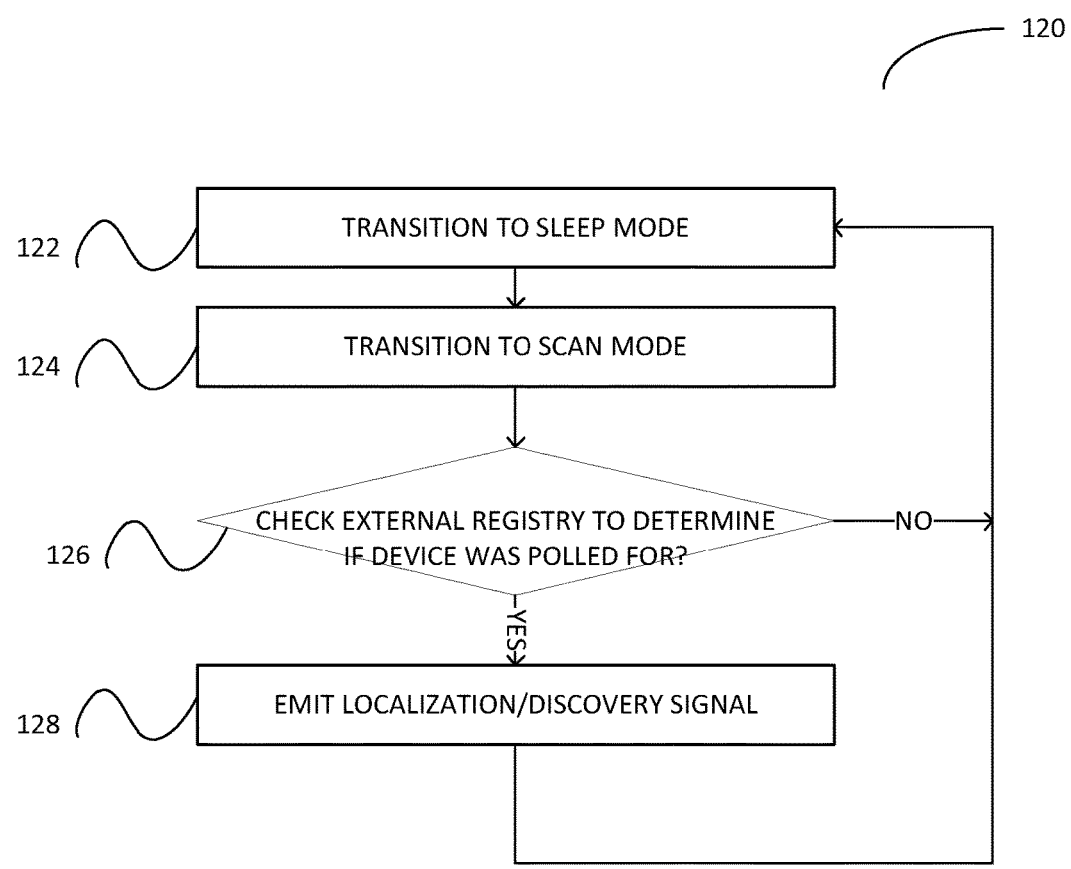

According to some embodiments, a method for localizing a medical device may be carried out such as method 120 of FIG. 1B. Steps 122,124 and 128 may be substantially similar to steps 102,104 and 108 (accordingly). While in scanning mode the medical device may continuously or intermittently check an external registry to determine if the medical device was polled for (as shown in step 126). For example, the medical device may broadcast, transmit or emit an identifier associated with the specific medical device to a computing platform. The computing platform may include a log storing all medical devices being sought out. The identifier may be a wireless packet associated with a specific medical device, may be an IP address or otherwise. Thus the computing platform may compare the medical device identifier to sought medical device(s) identifiers and signal a confirmation if there is a correlation or match. The medical device may activate a beacon if a confirmation is received from the computing platform (step 128).

Figure 1C:
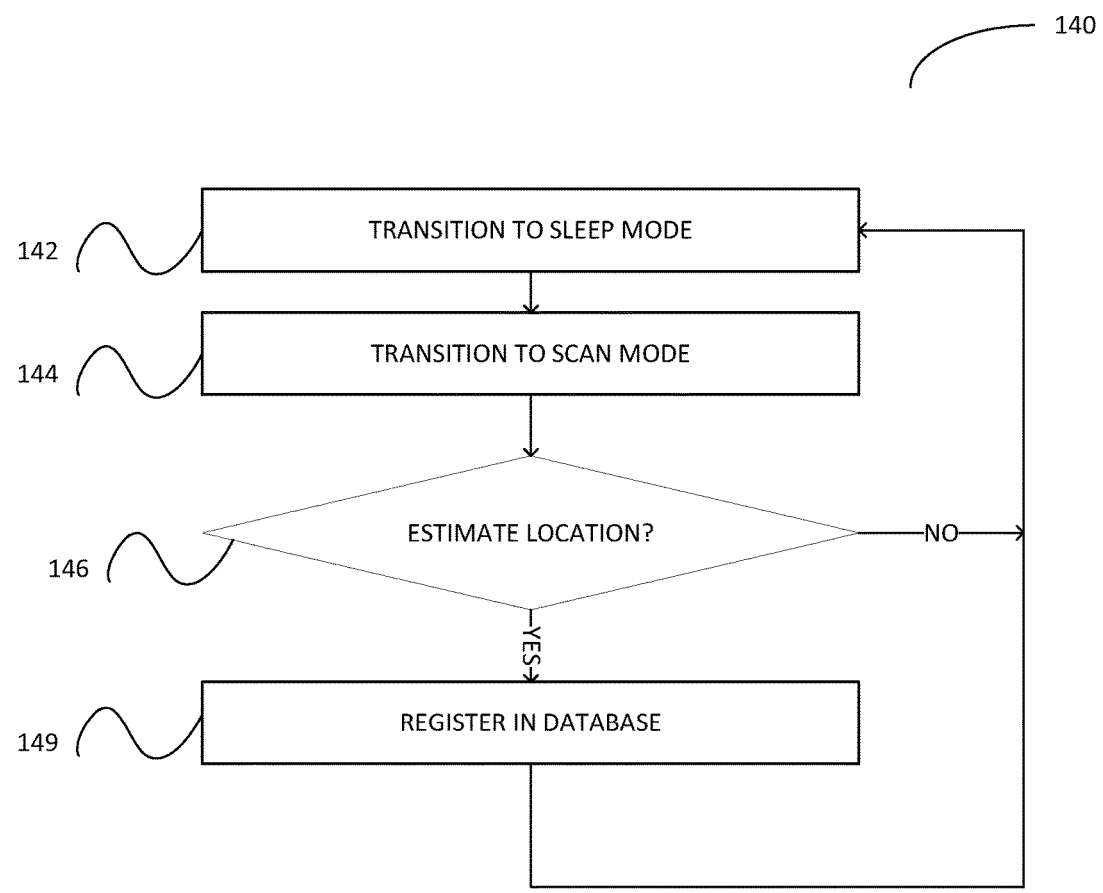

According to some embodiments, a method for localizing a medical device may be carried out such as method 140 of FIG. 1C. Steps 142 and, 144 may be substantially similar to steps 102 and 104 (accordingly). While in scanning mode the medical device may continuously or intermittently contact a computing platform or database within the vicinity of the medical device (as shown in step 146). The medical device may then register in the computing platform or database (step 149). Registration in the computing platform/database may include information such as status (such as the medical device currently in use), estimated location and/or operational logs associated with the medical device. An estimated location and secondary or associated information to an estimated location may include information such as nearby markers, an identifier of a nearby access point, computing platform or nearby additional medical device or may be calculated or detected by known wireless device location estimation methods such as access network received signals and characteristics of the signals (amplitude, strength, direction, correlation between two or more signals received), antenna triangulation or via a look up table correlating the computing platforms which detected a sought device and an estimated location associated with those devices. The access network may be Wi-Fi, RF, Bluetooth, cellular base-station identification, global position system (GPS) information, cellular triangulation, Hotspots or other methods of detecting or tracking movement in a wireless device. Operational logs registered in the register may be information associated with the medical device operation such as drugs delivered, medical device operation rate, date/time of delivery, duration of operation, patient ID and more. Not depicted are subsequent steps of activating a beacon although it is understood that such steps may be subsequent to the logging, for example, when a seeking device identifies the medical device within the log.

Figure 1D:
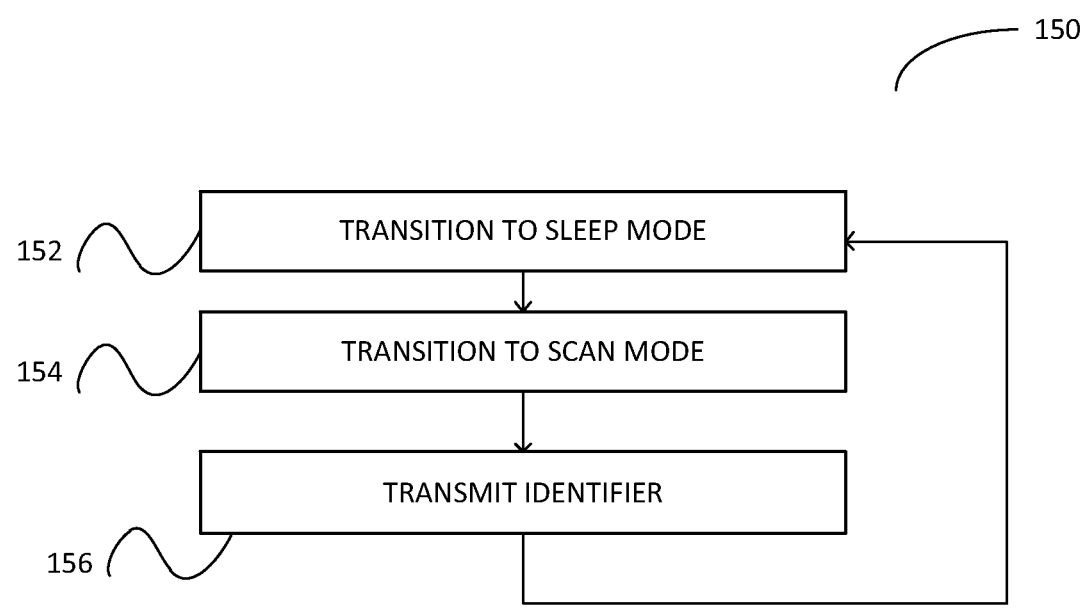

According to some embodiments, a method for localizing a medical device may be carried out such as method 150 of FIG. 1D. Steps 152 and 154 are substantially similar to steps 102 and 104 (accordingly). Method 150 may further include the step of transmitting/broadcasting an identifier associated with the medical device. Step 156 may be repeated several times before transitions to sleep mode. Such a method may be utilized to identify medical devices within a vicinity, for inventory control and more.

Figure 1E:
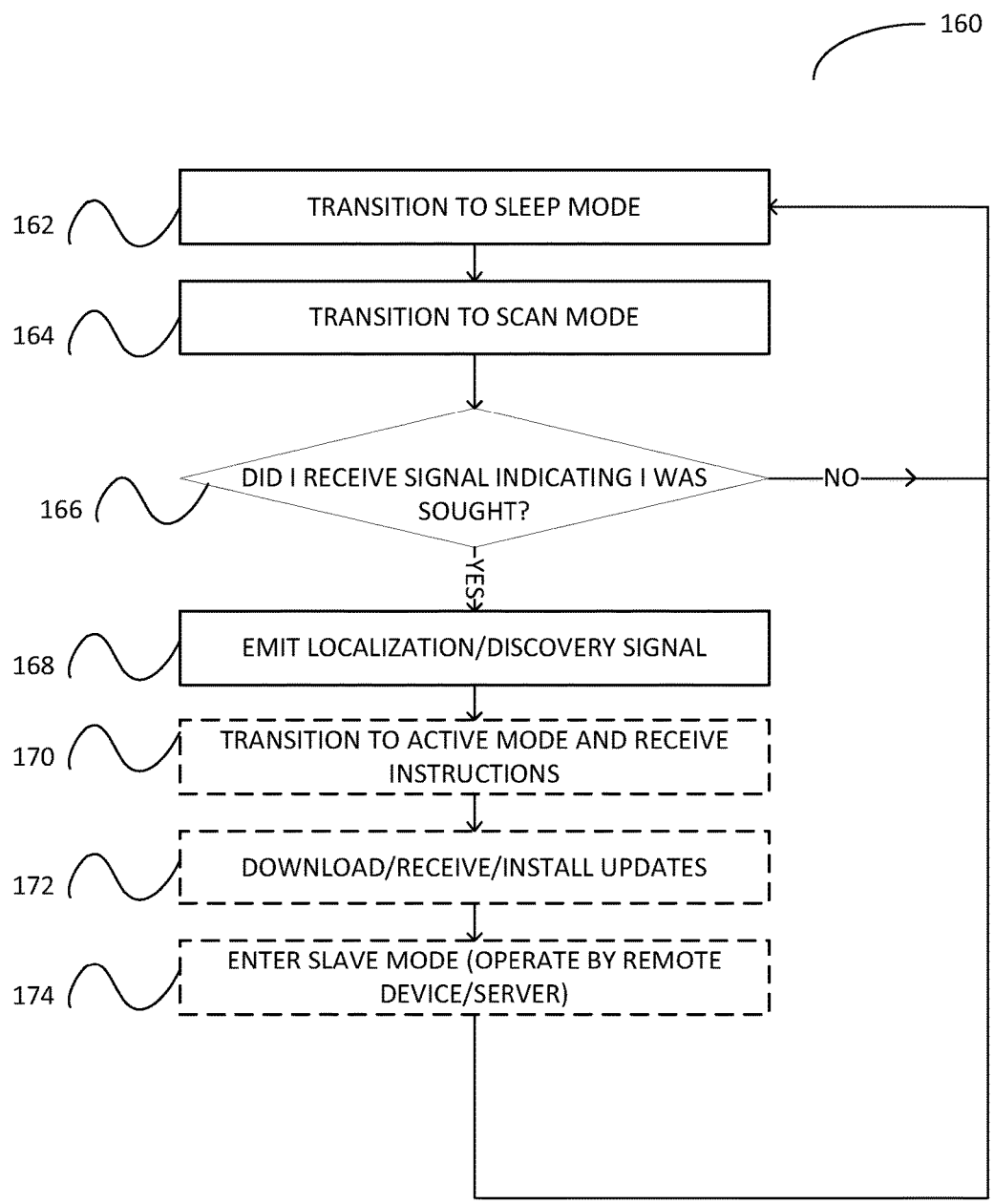

According to some embodiments, a method for localizing a medical device may be carried out such as method 160 of FIG. 1E. Steps 162,164 and 168 may be substantially similar to steps 102, 104 and 108 (accordingly). Step 166 may be substantially similar or interchangeable with steps 106,126, 146 and/or 149. Method 160 may further include the step of transitioning to an active mode and receiving a beacon from a poling/seeking device in the vicinity of the medical device (step 170). Optionally, method 160 may further include the step of downloading, receiving or installing updates associated with the medical device and its functionality such as drug libraries, operational regimes and more (step 172). Optionally, method 160 may further include the step of entering into a slave mode wherein the medical device is at least partially activated or controlled by a remote device or server functioning as a master device (step 174). According to some embodiments step 174 may include control of one medical device by an additional medical device and/or coordination between two or more devices by a server facilitating coordination between multiple medical devices servicing a given patient or set of patients.

Figure 2:
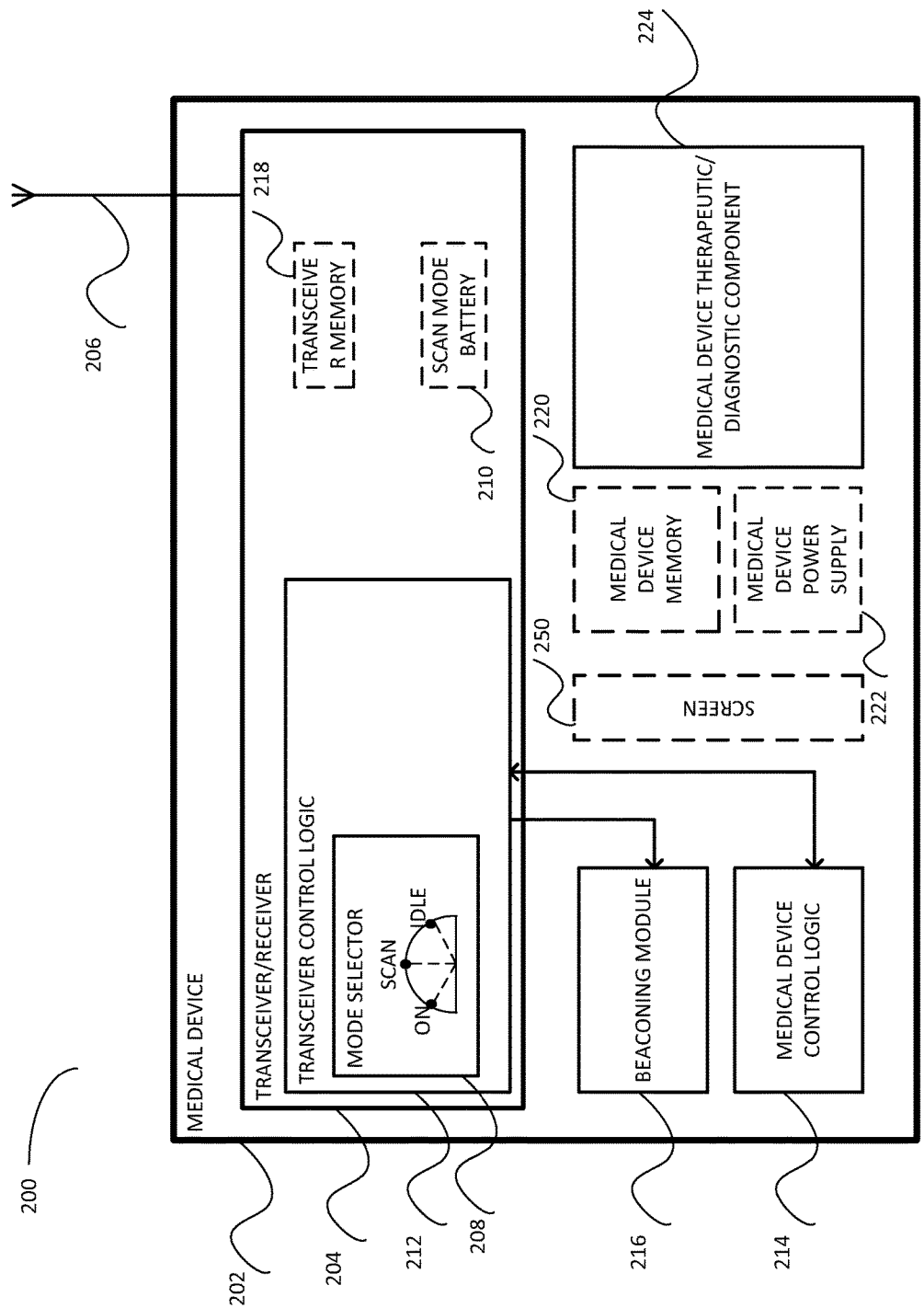
FIG. 2 is a functional block diagram of an exemplary medical device communication, control and localization apparatus according to embodiments of the present invention.

Turning now to FIG. 2, depicted is a functional block diagram of an exemplary medical device communication, control and localization apparatus such as apparatus 200 according to embodiments of the present invention. Apparatus 200 may include a medical device such as medical device 202 configured to carry out a medical treatment or therapeutic regiment. Medical device 202 may include a receiver or a transceiver such as transceiver 204 configured to receive a wireless transmission. Transceiver 204 may further be configured to transmit a wireless transmission. Transceiver 204 may include one or more antennas such as antenna 206. Antenna 206 may be a printed antenna, chip antenna, extender antenna and more. Transceiver 204 may be a radio frequency (RF), Wi-Fi, wireless internet, cellular, GPS and/or other transceiver. Transceiver 204 may include a mode selector such as mode selector 208 configured to cause/enable transceiver 204 to alternate between a scan mode, sleep mode and active/awake/on mode. In the active mode medical device 202 is in its operative mode for carrying out a medical use. In its sleep mode medical device 202 is in a battery/energy saving mode where most circuits are shut off or in a sleep mode. In its scan mode the transceiver's circuits may be activated or turned on to: (1) listen for wireless signals/packets addressed to the transceiver identifier, (2) wirelessly transmit/broadcast its own identifier, (3) wirelessly connect to and check a registry of a computing platform and more. Transceiver 204 may further comprise a dedicated battery such as scan mode battery 210 which may be a rechargeable battery, a capacitor and more. Battery 210 may recharge when connected to an external power supply. Battery 210 may be configured or chosen so that the ratio between its full/maximal charge capacity and passive discharge rate (for example due to leakage) is above a threshold so that transceiver operation may be operative for at least 4 months and/or for at least 6 months.

According to some embodiments, battery 210 may be sufficient to power the transceiver to alternate between a sleep mode and a scan mode and operate in the scan mode (emit signal, listen for packets and more) for over 4 months. For example, a battery may have a full charge capacity and a passive discharge rate (for example due to standby leakage) whose rate is above a threshold value. The battery may be selected so that the transceiver is operable with a power supply from the battery for at least 4 months and/or at least 6 months. Furthermore, it is understood that the system design and low power consumption of the transceiver functionality may enable using a standard battery.

According to some embodiments, transceiver 204 may further include a control logic such as transceiver control logic 212. Transceiver control logic 212 may include, be embedded with or be operable with mode selector 208. Transceiver control logic 212 may be a circuit or code/thread running on a general purpose controller. Transceiver control logic 212 may be dedicated for the transceiver or may be joint with a medical device control logic such as medical device control logic 214. Mode selector 208 may control/indicate to the medical device control logic (214) to switch to an on or active mode. Transceiver control logic 212 may be configured to transition operation of the transceiver between modes (such as on, sleep and scan modes). Transceiver control logic may further include a timer and/or sleep/wake circuits.

According to some embodiments, medical device 202 may include a localization module such as beaconing module 216 configured to emit a guiding signal, for example, when medical device 202 is acknowledged as being sought. Exemplary guiding signals are: a beacon, alarm, flashing light, colored light, a signal transmitted by transceiver 204 to indicate location of medical device 202, a combination of the exemplary guiding signals and more. Beaconing module 216 may be included within or external to the transceiver 204.

According to some embodiments, medical device 202 may include one or more memory modules such as transceiver memory 218 and/or medical device memory 220. Optionally, the two memories 218 and 220 may be joined, embedded or separated. Transceiver memory 218 may be stored within the transceiver and may further be configured to be turned on in scan mode to allow access to relevant information needed in that mode such as location information. Memory 218 and/or 220 may store treatment regiments associated with the medical device, coordination regiments between the medical device and an associated medical device, location associated information (such as closest medical device detected, closest hot spot detected, location coordinates) and more.

According to some embodiments, medical device 202 may include a medical device power supply such as medical device power supply 222 which may be a rechargeable battery, a power source or connectivity to an electrical socket and more. Medical device power supply 222 may be combined with or separate from scan mode battery 210.

According to some embodiments, medical device 202 may include medical device therapeutic/diagnostic portion circuit or assembly such as component medical device therapeutic/diagnostic component 224 and may be configured to carry out the therapeutic or diagnostic operations/functionality of the medical device such as a medical pump, a blood pressure measurement apparatus, heart and lung machine, a dialysis machine, a cat scan, an x-ray machine and more. Medical device therapeutic/diagnostic component 224 may be controlled by medical device control logic 214.

According to some embodiments, medical device 202 may further include a screen such as screen 250 which may be a color screen, black and white screen, touch screen, flat screen and/or otherwise. Screen 250 may be configured to display a flag indicative of a non-discovery condition. For example, if medical device 202 was located but was not subsequently discovered (for example, physically located by a user) a flag or notification with relevant information such as: contact information, when the medical device was sought and more may be displayed on the screen so that a subsequent user may choose to notify a person/system seeking the medical device where it is located.

Figure 3:
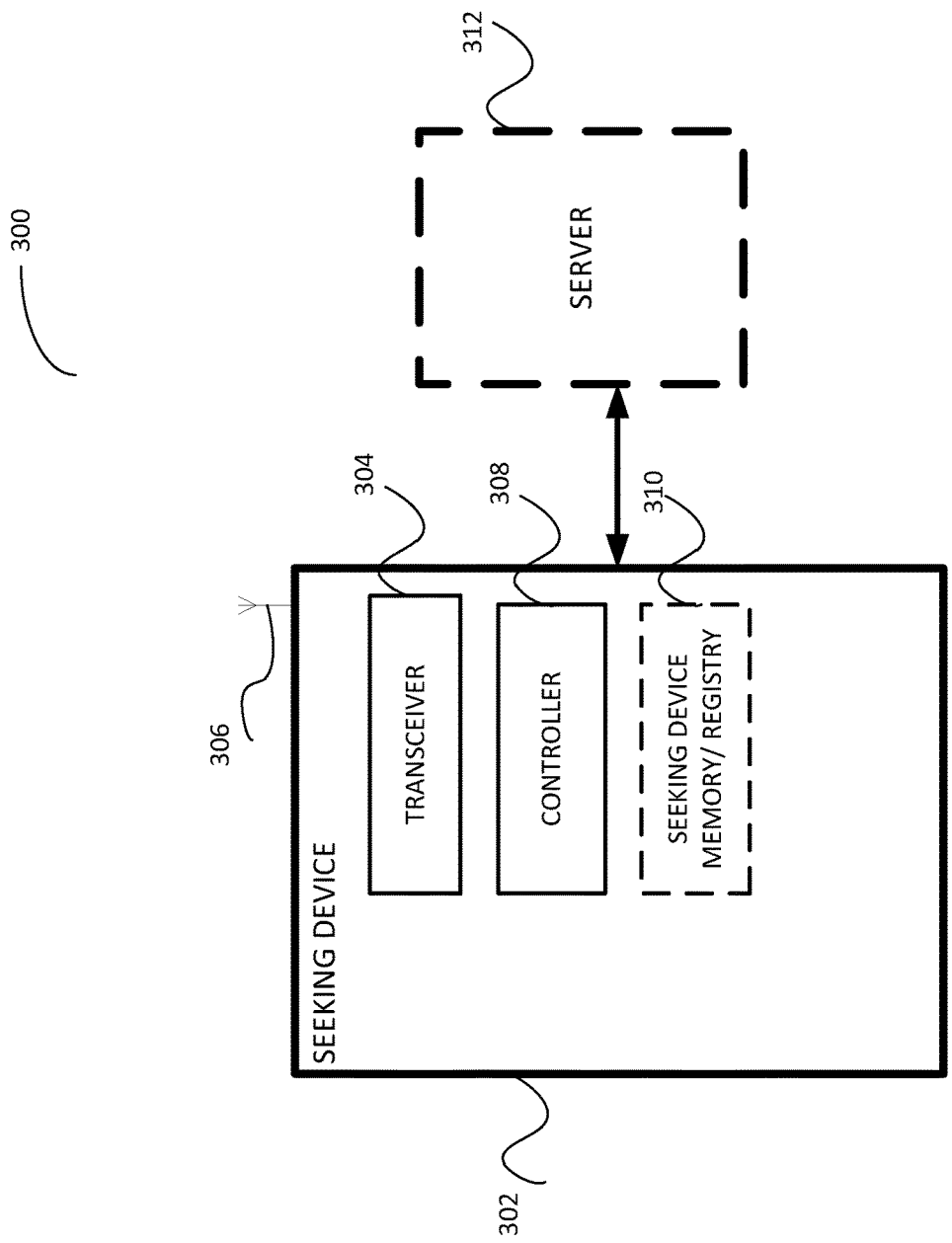
FIG. 3 is a functional block diagram of an exemplary computing platform operable to seek for a medical device according to embodiments of the present invention.

Turning now to FIG. 3 depicted is a functional block diagram of an exemplary computing platform such as computing platform 300 operable to seek for a medical device according to embodiments of the present invention. Computing platform 300 may include a seeking device such as seeking device 302. Seeking device 302 is operable to seek for medical devices such as described with regard to FIG. 2 but not limited to this example. Seeking device 302 may include a transceiver such as transceiver 304 including an antenna such as antenna 306 and a controller such as controller 308. Seeking device 302 may further include a computing platform memory or registry such as memory 310. Transceiver 304 may be a radio frequency (RF), Wi-Fi, wireless internet, cellular, GPS and/or other transceiver operable to receive and transmit signals from transceiver 204. Computing platform 300 may include a server such as server 312 which may be associated wirelessly or otherwise with seeking device 302 and additional seeking devices. Controller 308 may be configure to enable to operate transceiver 304 to: (1) emit a polling or seeking signal for one or more medical devices, (2) register medical devices detected within proximity to the computing platform in the memory 310, (3) compare a registry/list from memory 310 or server 312 of detected medical devices to a sought medical device and send a confirmation to the medical device if it is sought by a user and more.

According to some embodiments, server 312 may be one or more servers. Server 312 may be configured to manage, coordinate or operate a plurality of seeking devices. Server 312 may include a memory for storing and managing which medical devices were detected, where medical devices are located, which seeking devices are in proximity to a medical device, which medical devices are being polled for and more. Server 312 may further be configured to manage wireless updates of medical devices such as: drug library updates and associated information, system updates and associated information, Firmware updates, operational modes/regimes updates, drug libraries updates. Server 312 may be configured to facilitate wireless connection between multiple medical devices servicing a given patient or set of patients.

Figure 4B:
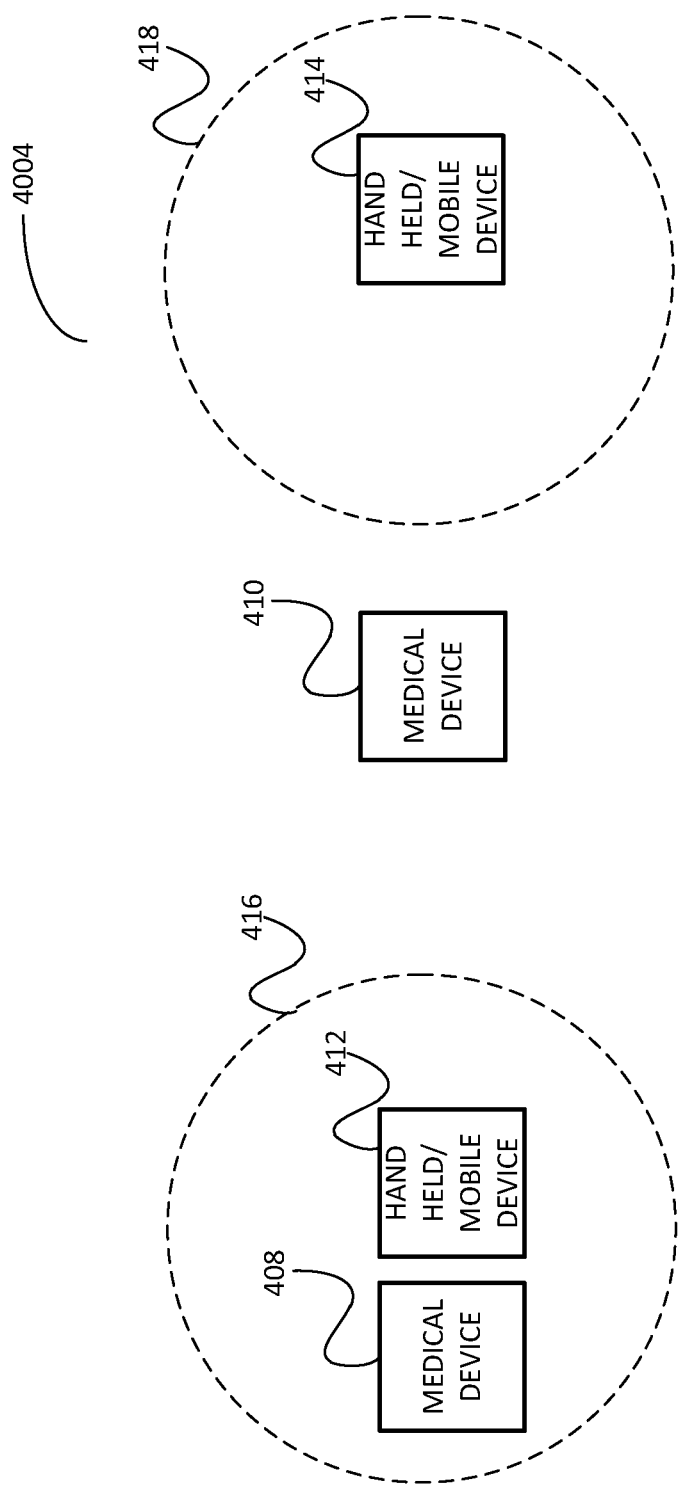

Turning now to FIG. 4A-4E are schematic illustrations, depicting exemplary medical device communication, control and localization systems according to embodiments of the present invention. FIG. 4A depicts a first exemplary medical device communication, control and localization configuration such as system 4002. System 4002 may include one or more medical devices such as medical devices 402 and 404. Medical devices 402 and 404 may be identical, similar or different types of medical devices. Medical device 402 may function as a medical device as described in FIG. 1A-1E. Medical device 404 may function as wireless polling or seeking device as described above. Medical device 402 may be wirelessly polled for by medical device 404 and when found the two medical devices may create a direct wireless connection or optionally, utilize a hub or additional server such as hub/server 406 to maintain wireless connection between each other. The connection between medical devices 402 and 404 may allow the two medical devices to coordinate treatments between themselves.

According to some embodiments, the use of medical device 404 and additional (not shown here) medical devices as computing platforms or seeking devices may allow creation of an ad hoc grid of polling devices seeking other medical devices. Exemplary embodiments utilizing this configuration could be field hospitals or hospitals lacking sufficient hot spots to increase the amount of seeking devices, or substantially immobile medical devices being used to identify nearby mobile medical devices in their proximity.

Turning now to FIG. 4B, depicts a second exemplary medical device communication, control and localization configuration system according to embodiments of the present invention such as system 4004. System 4004 includes two medical devices such as medical devices 408 and 410 which each may function as described in FIG. 1A-1E. Seeking devices such as hand held/mobile devices 412 and 414 may seek medical devices within their coverage areas 416 and 418 (respectively). A hand held/mobile device may find a medical device if it is within its coverage area so that hand held/mobile device 412 may find medical device 408 while neither hand held/mobile devices 412 nor 414 may find medical device 410 and is thus not found. Hand held/mobile devices 412 and 414 may be personal digital assistant (PDA), tablets, smart phones or cellular phones, laptop computers, barcode scanner joint with a wireless transceiver and more.

Figure 4C:
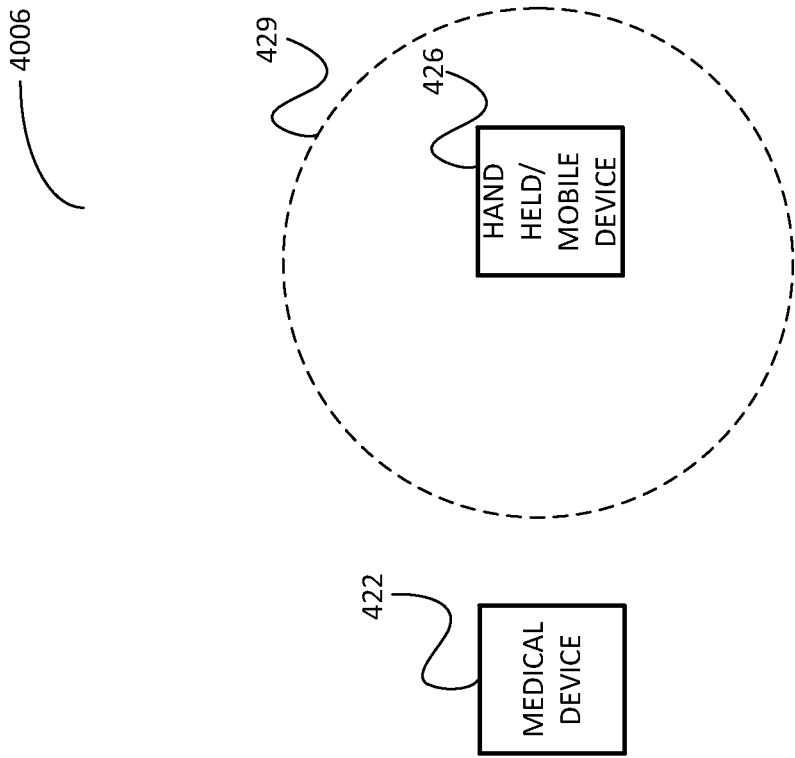
Figure 4C:
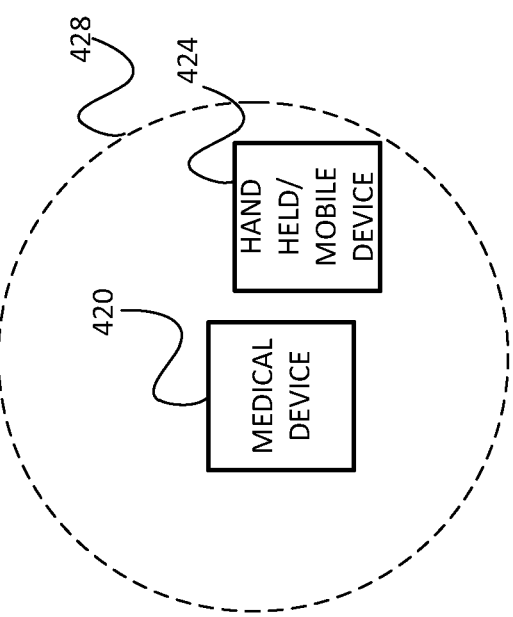

Turning now to FIG. 4C, depicted is a third exemplary medical device communication, control and localization configuration system according to embodiments of the present invention such as system 4006. System 4006 is substantially identical to system 4004, elements 420-426 may be substantially identical to elements 408-414 (accordingly). A medical device may register or contact a seeking device if it is within its coverage area (428 and 429) so that medical device 420 may contact hand/held mobile device 424 while medical device 422 does not contact hand held/mobile devices 424 or 426 and is thus may not be detected.

In some exemplary embodiment in accordance with FIGS. 4B and/or 4C may be for home use or home care medical devices distributed to patients to be used in their homes, a misplaced medical device can be located within a patient's home using a hand held seeking device. In a different example, field hospitals may utilize hand held devices to locate misplaced or missing medical devices. In a different example, hospitals may use hand held devices to locate medical devices, a map covering target areas covering parts or all of a hospital can be planned so that sought medical devices (for example 408 and 410) can be found throughout the hospital. For example, a worker may be supplied with a map of places to stand for predefined periods of time so that the whole hospital is eventually covered by coverage areas (for example 416) of the hand held device so that all sought medical devices (for example 408 and 410) are subsequently located.

Figure 4D:
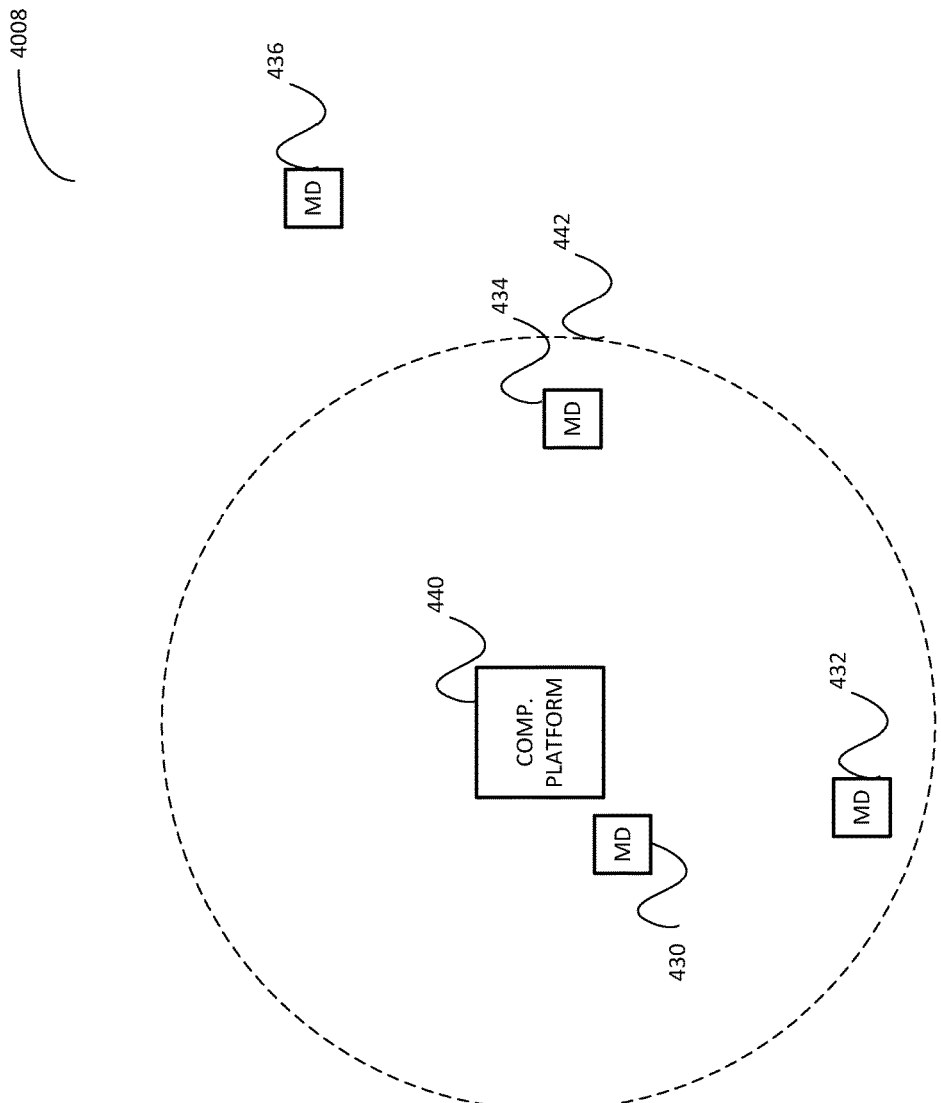

Turning now to FIG. 4D, depicted is a fourth exemplary medical device communication, control and localization configuration system according to embodiments of the present invention such as system 4008. System 4008 may include medical devices such as medical devices 430, 432, 434 and 436 and each may function as a medical device as described in any of FIG. 1A-1E. a computing platform such as computing platform 440 may poll for sought after medical devices 430-436. Medical devices within computing platform's coverage area 442 may be detected (in this example, medical devices 430-434) while medical device 436 is not. An exemplary embodiment for this configuration may be a nurse's station including a Wi-Fi transmitter and a computer or docking station functioning as the computing platform 440 polling for missing medical devices 430-436 within the ward covered by coverage area 442. A similar configuration depending on a medical device's coverage area as described with regard to FIG. 1C may also be configured.

Figure 4E:
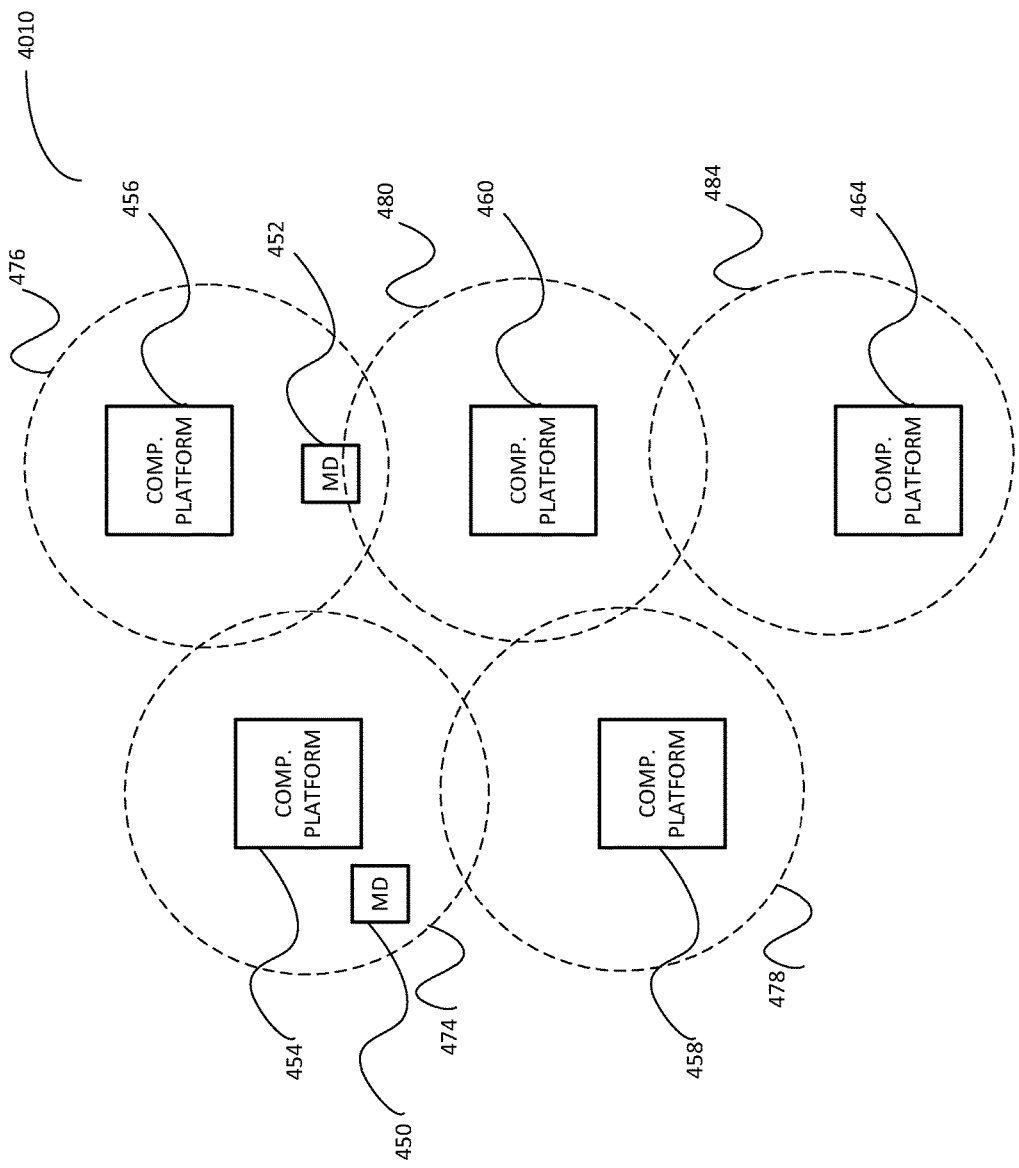

Turning now to FIG. 4E, depicted is a fifth exemplary medical device communication, control and localization configuration system according to embodiments of the present invention such as system 4010. System 4010 may include medical devices such as medical devices 450 and 452, each may function as a medical device as described in any of FIG. 1A-1E. Computing platform such as computing platforms 454-464 may poll for sought after medical devices 450 and 452. Medical devices within computing platform's coverage areas 474-484 may be detected. The plurality of computing platforms 454-464 may create a grid covering some or all of a predetermined area and may provide additional information such as which computing platform the medical device is nearest to or improved accuracy of localization due to additional information. An exemplary embodiment for this configuration may be a nurse's station including multiple Wi-Fi transmitters throughout a hospital ward and a computer or docking station functioning as the computing platforms 454-464. Polling for missing medical device 450 within the ward is covered by coverage area 474 and polling for missing medical device 452 within the ward is covered by coverage areas 476 and 480. An additional exemplary embodiment may be a hospital covered by a computing platform grid such as created by computing platforms 454-464 to allow monitoring of medical devices within the grid to aid in inventory control of medical devices within the hospital. A similar configuration depending on medical device's coverage area as described with regard to FIG. 1C may also be configured, or that a grid or array created by a multiplicity of medical devices acting also as seeking devices may be implemented.

Figure 5A:
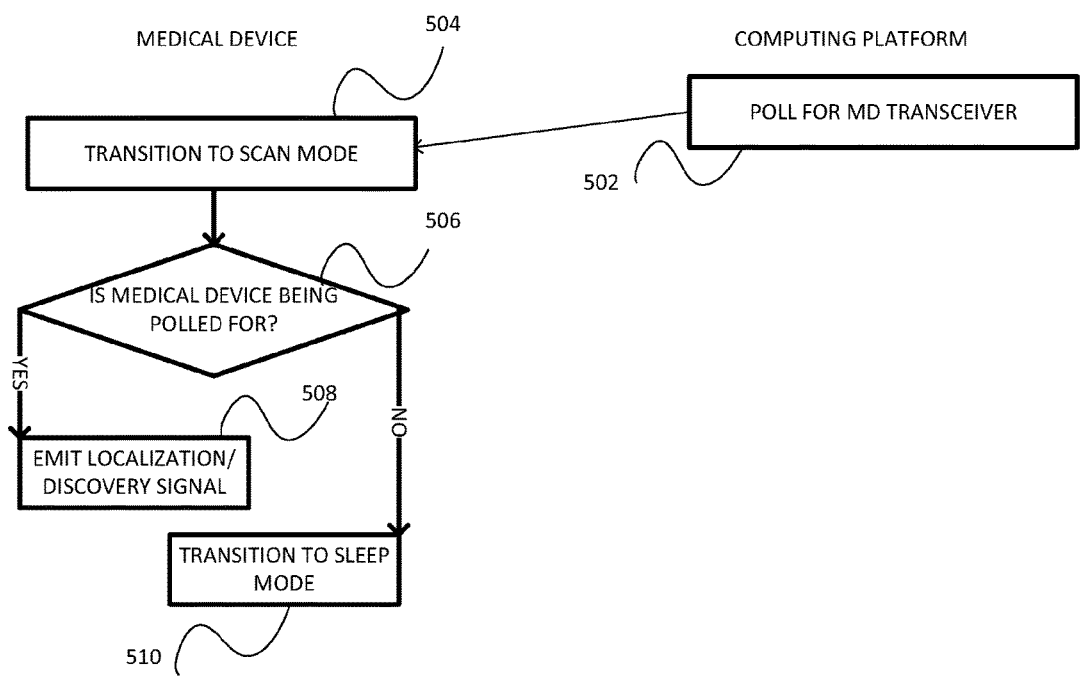
FIG. 5A-5C are flow charts including the exemplary steps associated with which may be performed by the exemplary medical devices and/or the medical device communication, control and localization system of FIGS. 2 and 3.
Figure 5B:
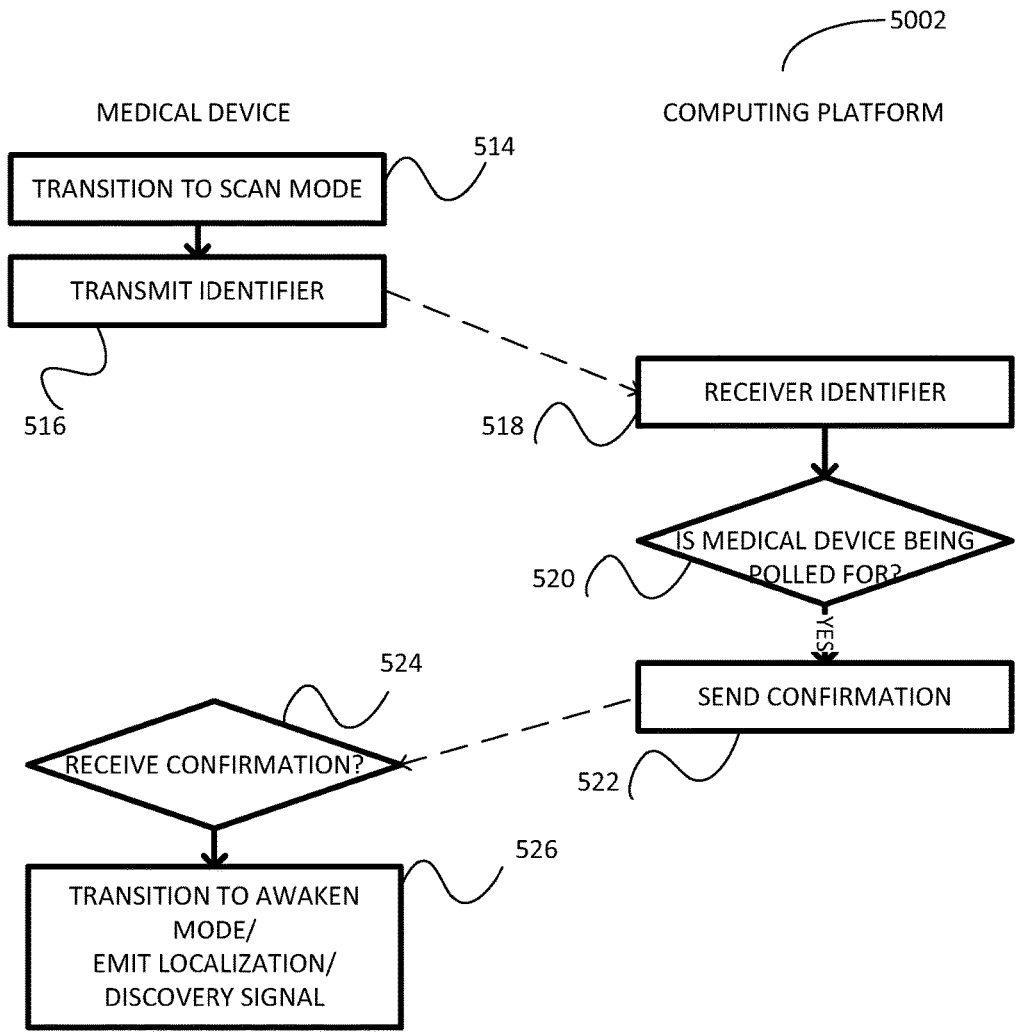
Figure 5C:
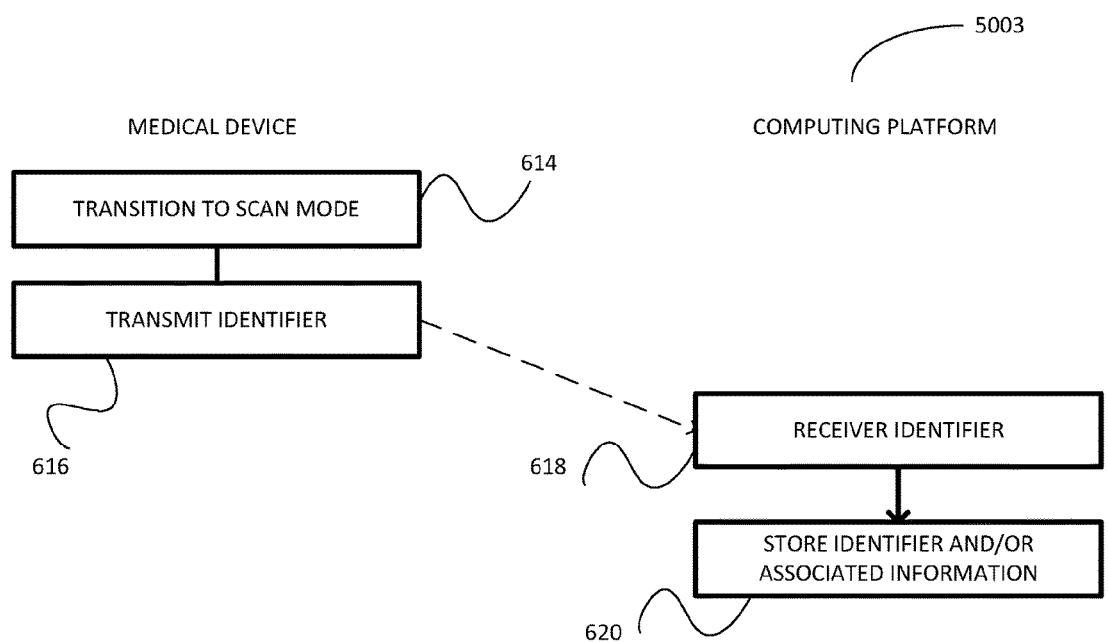

Turning now to FIG. 5A-5C depicted are flow charts including the exemplary steps associated with according to embodiments of the present invention which may be performed by the exemplary medical devices and/or the medical device communication, control and localization system of FIGS. 2 and 3. FIG. 5A depicts flow 5001 including a medical device and a computing platform exemplary steps. A computing platform may poll for one or more medical devices (step 502). The computing platform may intermittently poll for the sought after medical devices for example for a period of 10 minutes poll for all relevant medical devices every 2 seconds. The medical device may transition into a scan mode (step 504) for example once every 3.5 minutes or if the medical device is connected to an external power source the medical device may stay in a scan mode. The medical device may determine if it is being polled for (step 506) for example once every 5 seconds while in scan mode or continuously if connected to an external power source. Rate or frequency of transition into scan mode (step 504) and/or determining if being polled for (step 506) may also be programmed and modified from time to time, for example, a medical device may be programmed to transition into scan mode (step 504) once every 20 minutes and a system update may reprogram the medical device to transition into scan mode (step 504) once every 5 minutes during night hours (such as 8 pm to 4 am) and once every hour during daytime hours (such as 4 am to 8 pm). If a poll is received, the medical device may transition to an awaken mode for a predetermined length of time (for example 2 hours) and/or may activate a discovery signal (step 508). If a poll is not received the medical device may transition to a sleep mode (step 510) or if connected to an external power source may remain in scan mode.

FIG. 5B depicts flow 5002 including a medical device and a computing platform exemplary steps according to embodiments of the present invention. The medical device may transition into a scan mode (step 514) for example once every 3.5 minutes or if the medical device is connected to an external power source the medical device may stay in a scan mode. The medical device may transmit an identifier (step 516) for example once every 3.5 minutes or once every 5 seconds. A computing platform may receive the identifier (step 518) and determine if the medical device is being sought or polled for (step 520) and optionally may store the identifier in a database or register. If the medical device is being sought or polled for the computing platform may return/send a confirmation (step 522). Upon receipt of the confirmation (step 524) the medical device may transition to an awaken mode for a predetermined length of time (for example 2 hours) and/or may activate a localization signal (step 526).

FIG. 5C depicts flow 5003 including a medical device and a computing platform exemplary steps according to embodiments of the present invention. The medical device may transition into a scan mode (step 614) for example once every 3.5 minutes or if the medical device is connected to an external power source the medical device may stay in a scan mode. The medical device may transmit an identifier (step 616) for example once every 3.5 minutes or once every 5 seconds. A computing platform may receive the identifier (step 618) and store the identifier and or more information in the computing platform (step 620). For example, while managing an inventory it may be desirable to register all of the detectable medical devices. The medical devices may periodically or intermittently transmit their identifier and the computing platform may store the received identifiers in a registry or memory within a server. Furthermore, additional information such as which seeking device(s) received identifier from the medical device, when the identifier was received and more.

Figure 6:
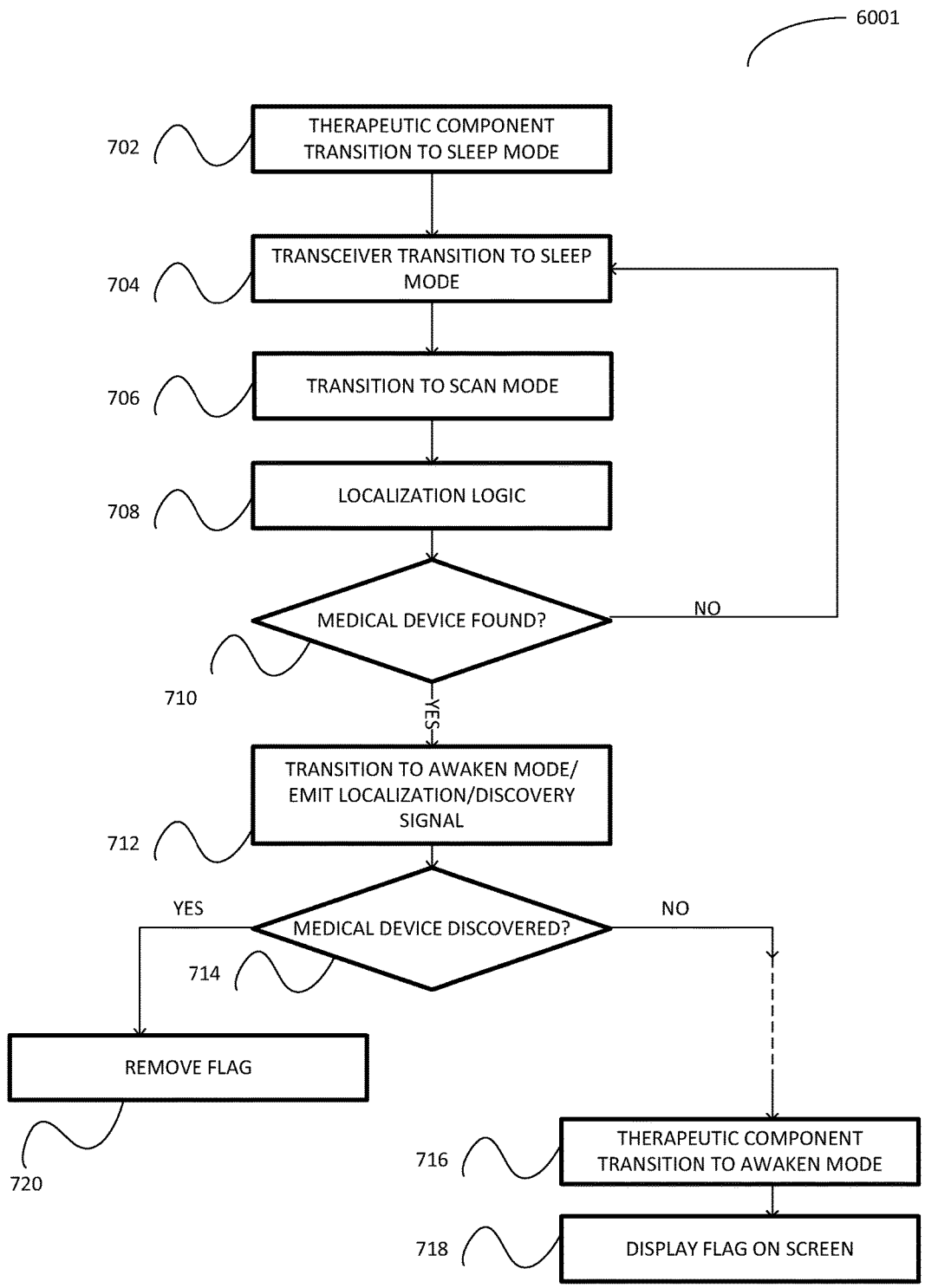
FIG. 6 is a flow chart including exemplary steps which may be executed by a transceiver and a therapeutic component according to embodiments of the present invention.

Turning now to FIG. 6, depicted is a flow chart (6001) including exemplary steps for a transceiver and a therapeutic component according to embodiments of the present invention. A therapeutic component of a medical device may transition into a sleep mode or a device sleep mode (DSM) wherein while the therapeutic functionality of the medical device is not active, the therapeutic component is turned off so as to save energy (step 702), Substantially concurrently with therapeutic component transitioning into a DSM the transceiver may transition into a transceiver sleep mode (TSM) (step 704) and periodically transition into a scan mode (step 706) as described above, for example, with regard to step 104 of FIG. 1A. The transceiver may then activate various localization methods (step 708) which may further be understood by steps 506 of FIG. 5A, step 526 and 524 of FIG. 5B, step 616 of FIG. 5C and more. If the medical device was found (step 710) the transceiver may transition into an awake mode and the therapeutic component may transition into a therapeutic mode and the medical device may further emit a discovery signal (step 712). If the medical device was not found, the transceiver may transition back to a TSM (step 704).

According to some embodiments, if the medical device was not discovered, for example the medical device was not physically found by a person, an audible beacon was not heard by a user seeking a medical device, or a computing platform remotely located did not receive/identify a substantially accurate location of the medical device (step 714), upon subsequent turning on of the medical device (step 716) by a user a flag may be displayed on a screen with information such as when the medical device was sought for, who was seeking for the medical device and contact information so that the user may notify of the location of the medical device (step 718). It is to be understood that step 716 may be a spontaneous event and may not take place chronologically after step 714 for example but rather, whenever step 714 occurs if the medical device was found (step 710) and not discovered (step 714) a flag indicative of a non-discovery condition may appear on the screen. If the medical device was discovered (step 714) then the flag may be removed or confirming of discovery may be completed (step 720) either electronically (for example, a signal is received) or mechanically (for example, a mechanical switch is set) and either automatically (for example if the seeking device confirm finding) or manually (for example a user confirms finding). According to some embodiments the flag may further be displayed on a screen (step 718) concurrently with emitting of a detection symbol.

According to some embodiments, if therapeutic component is active, for example, administering a treatment the transceiver will not transition to a seeking mode and/or may not respond to a poll. A flag may be displayed (step 718) in such a situation, once the therapeutic component transitions to a non-active mode or once the therapeutic component subsequently awakens. According to some embodiments discovering a medical device (step 714) may include hearing or seeing a beacon emitted from the medical device and physically locating/finding the medical device by a person.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed:
1. A system for localizing medical devices, said system comprising:

a medical device comprising:
  a therapeutic component;
  a wireless transceiver;
  wherein said medical device is configured to deactivate said therapeutic component and said wireless transceiver during a deep sleep mode of said medical device;
  a controller configured to periodically initiate, when said medical device is in the deep sleep mode, a scan mode, in which said controller:
    a. activates said transceiver and causes said transceiver to:
      i. transmit a first wireless signal carrying an identifier associated with said medical device;
      ii. scan for a second wireless signal indicating a localization request addressed to said medical device; and
      iii. signal said controller if the second wireless signal is detected;
    b. in the event the second wireless signal is detected, cause said medical device to emit a localization signal; and
    c. in the event a wireless signal indicating a localization request addressed to said medical device is not detected within a pre-defined time period, cause said medical device to return to the deep sleep mode;
and
a computing platform comprising:
  a registry of identifiers of sought after medical devices; and
  communication circuitry for receiving the first wireless signal transmitted by said medical device and transmitting a localization request addressed to said medical device if the identifier carried by the first wireless signal matches an identifier of a sought after device in said registry.

2. A system according to claim 1, wherein said controller is adapted to initiate the scan mode at pre-defined time intervals, when said medical device is in the deep sleep mode.

3. A system according to claim 1, wherein said computing platform is further configured to derive locational data of said medical device from the first wireless signal.

4. A system according to claim 3, wherein said computing platform is further configured to record the derived locational data, such as to maintain a listing of current locations of a set of medical devices including said medical device.

5. A system for localizing medical devices, said system comprising:
  a set of medical devices, each having alternative operating modes including a deep sleep mode, a scan mode and an active mode, each of said medical devices comprising:
    a therapeutic component;
    a wireless transceiver;
    wherein each of said medical devices is configured to deactivate said therapeutic component and said wireless transceiver during the deep sleep mode;
    a controller configured to periodically initiate, when said medical device is in the deep sleep mode, the scan mode, in which said controller:
      a. activates said transceiver and causes said transceiver to:
        i. transmit a first wireless signal carrying an identifier associated with said medical device;
        ii. scan for a second wireless signal indicating a request addressed to said medical device; and
        iii. signal said controller if the second wireless signal is detected;
      b. in the event the second wireless signal is detected, cause said medical device to transition to the active mode and receive instructions; and
      c. in the event a wireless signal indicating a request addressed to said medical device is not detected within a pre-defined time period, cause said medical device to return to the deep sleep mode;
  and
  a computing platform comprising:
    a registry of identifiers of said set of medical devices;
    communication circuitry for receiving the first wireless signals transmitted by said medical devices and deriving a location of each of said medical devices from the first wireless signals;
    a listing of current locations of each of the medical devices, compiled and updated based on the received first wireless signals;
    communication circuitry for transmitting requests addressed to said medical devices, each timed to match a scan mode of a respective medical device of said set of medical devices by transmitting the requests in response to receiving the first wireless signal from the respective medical device.

6. A system according to claim 5, wherein said controller is adapted to initiate the scan mode at pre-defined time intervals, when said medical device is in the deep sleep mode.

7. A system according to claim 5, wherein said instructions are configured to cause said medical device to receive a software update from said computing platform.

8. A system according to claim 5, wherein said instructions are configured to cause said medical device to activate a therapeutic functionality.

9. A system according to claim 5, wherein said instructions are configured to cause said medical device to transition to a slave mode, allowing remote control of said medical device.

10. A self-localizing medical device comprising:
  a therapeutic component;
  a wireless transceiver;
  wherein said medical device is configured to deactivate said therapeutic component and said wireless transceiver during a deep sleep mode of said medical device;
  a controller configured to periodically initiate, when said medical device is in the deep sleep mode, a scan mode, in which said controller:
    a. activates said transceiver and causes said transceiver to:
      i. transmit a first wireless signal carrying an identifier associated with said medical device to a computing platform containing a registry of sought after medical devices;
      ii. scan for a second wireless signal transmitted by the computing platform indicating the identifier associated with said medical device is listed in the registry of sought after devices; and
      iii. signal said controller if the second wireless signal is detected;
    b. in the event the second wireless signal is detected, cause said medical device to emit a localization signal; and
    c. in the event a wireless signal, indicating the identifier associated with said medical device is listed in the registry of sought after devices, is not detected within a pre-defined time period, cause said medical device to return to the deep sleep model.

11. A device according to claim 10, wherein said controller is adapted to initiate the scan mode at pre-defined time intervals, when said medical device is in the deep sleep mode.

\* \* \* \* \*